United States Patent [19]

Bajpai

[11] Patent Number: 4,668,295
[45] Date of Patent: May 26, 1987

[54] SURGICAL CEMENTS

[75] Inventor: Praphulla K. Bajpai, West Carrollton, Ohio

[73] Assignee: University of Dayton, Dayton, Ohio

[21] Appl. No.: 726,868

[22] Filed: Apr. 25, 1985

[51] Int. Cl.⁴ .............................................. C04B 7/32
[52] U.S. Cl. ...................................... 106/85; 106/90; 106/95; 106/97; 106/104; 106/243
[58] Field of Search ............... 523/116; 106/119, 104, 106/243, 90, 95, 97, 85

[56] References Cited

U.S. PATENT DOCUMENTS

| | | | |
|---|---|---|---|
| 4,123,416 | 10/1978 | Potter et al. | 260/42.18 |
| 4,192,021 | 3/1980 | Deibig et al. | 3/1.9 |
| 4,209,434 | 6/1980 | Wilson et al. | 523/116 |
| 4,271,057 | 6/1981 | Drake et al. | 260/29.6 |
| 4,342,677 | 8/1982 | Maramatsu et al. | 523/116 |
| 4,527,979 | 7/1985 | McLean et al. | 523/116 |
| 4,542,167 | 9/1985 | Aoki | 523/116 |

FOREIGN PATENT DOCUMENTS 2929121  1/1980  Fed. Rep. of Germany ...... 523/116

OTHER PUBLICATIONS

"Experimental Studies on the Implantation of Hydroxyapatite in the Medullary Canal of Rabbits", First World Biomaterials Congress Baden near Vienna, Austria, Apr. 8-12, 1980, by S. Niwa et al.

"The Influence of Compositional Variations on Bone Ingrowth of Implanted Porous Calcium Aluminate Ceramics", J. Biomed. Mater. Res. Symposium, No. 6, pp. 17-22, (1975), by G. A. Graves et al.

Primary Examiner—Paul R. Michl
Assistant Examiner—Alex H. Walker
Attorney, Agent, or Firm—Biebel, French & Nauman

[57] ABSTRACT

Surgical bone repair cements useful in medical and/or dental applications comprising a bone substitute such as hydroxyapatite, tricalcium phosphate or aluminocalcium oxide-phosphorous pentoxide ceramic and a polyfunctional carboxylic acid such as malic acid, α-ketoglutaric acid or citric acid as a setting agent.

21 Claims, No Drawings

SURGICAL CEMENTS

BACKGROUND OF THE INVENTION

The present invention relates to surgical cements such as bone and dental cements. More particularly, it relates to a surgical cement of controllable setting time which comprises a powdered or granulated bone substitute and a non-toxic, water soluble, low molecular weight polyfunctional carboxylic acid as a setting agent.

Surgical cements are used in numerous medical and/or dental applications including in repairing bone fractures, in attaching bone plates and other protheses, in bridging comminuted fractures, and in filling or aligning dental cavities. Examples of such compositions are described in U.S. Pat. No. 4,123,416 to Potter et al.; U.S. Pat. No. 4,271,057 to Drake et al.; and U.S. Pat. No. 4,376,835 to Schmitt et al. Granulated products are commonly used as bone substitute materials in dental and orthopaedic applications. These materials work well; however, the particles tend to migrate from the surgical site or exfoliate into the mouth in the case of oral surgery. Typically, surgical cements are mixtures of a ceramic and a polymeric material. The polymeric materials most commonly used are poly(meth)acrylic acid, polyglycolic acid and polyactic acid.

Potter et al. disclose that the gel and setting times of a surgical cement containing a fluorosilicate glass can be varied by the addition of an organic dicarboxylic acid such as tartaric acid. For this purpose, the acids are only used in an amount of 5 to 15% by weight based on the weight of the polymer.

SUMMARY OF THE INVENTION

A principal object of the present invention is to provide a novel, fast setting, relatively strong, surgical cement composition.

The present invention describes a family of compounds that can be used to "set" or harden bone substitutes. This is of great utility to the surgeon for ease of application and for retaining the bone substitute at the surgical site. It is important that the setting agents described in this invention are completely biocompatible, water soluble and transitory. Such setting agents are absorbed by the body without significantly altering the desirable characteristics of the base bone substitute.

The surgical cement composition of the present invention comprises a powdered or granulated bone substitute and a water soluble, low molecular weight polyfunctional carboxylic acid.

DETAILED DESCRIPTION OF THE INVENTION

The polyfunctional carboxylic acids used in the present invention are to be distinguished from the polymeric materials previously used in surgical cements. They are not polymers, but water soluble, relatively low molecular weight compounds having two or more carboxyl groups. These acids tend to react very quickly with the bone substitute and thereby provide a very fast setting composition. Certain of the acids used in the present invention are found in the Kreb's cycle and are particularly desirable from the standpoint of their biocompatibility.

The water soluble, polyfunctional acids most typically used in the present invention are monomeric and contain from about 2 to 10 carbon atoms and, more particularly, 2 to 6 carbon atoms, and have 2 to 4 carboxyl groups. The polyfunctional carboxylic acids may be saturated or unsaturated. Representative examples of these acids include citric acid, $\alpha$-ketoglutaric acid, pyruvic acid, oxalic acid, tartaric acid, succinic acid, fumaric acid, malic acid, oxalacetic acid, etc. Preferred polyfunctional acids appear to be acids having a pK (first proton) less than 5.0. The most preferred acids are hydroxy acids such as malic acid and $\alpha$-ketoglutaric acid. The acids may be used alone but are advantageously used in combination to control setting properties. If the acids are solid, they preferably have a particle size less than 100 microns for homogenous dispersion.

The composition of the surgical cement will vary with its application. Some applications require more or less viscous compositions while others require faster or slower setting times. Typically the compositions of the present invention contain about 25 to 100 parts by weight polyfunctional carboxylic acid per 100 parts by weight of the bone substitute.

The term "bone substitute" as used herein includes both resorbable and non-resorbable biomaterials. It includes re-claimed bone mineral such as hydroxyapatite, corraline hydroxyapatite, $\beta$-Whitlockite; synthetic calcium compounds such as calcium aluminates and calcium phosphates; alumino-calcium ceramics such as alumino-calcium oxide-phosphorous pentoxide ceramics (ALCAP); tricalcium phosphate (alpha and beta); milled freeze dried bone and other materials useful as bone substitutes in surgical cements.

Among the substitutes that are useful in the present invention are Calcitite 2040, a commercially available, non-resorbable, synthetic hydroxyapatite available from Calcitek, Inc. of San Diego, Calif.; Biogel, a hydroxyapatite produced by Bio Rads Lab of Richmond, Calif.; the ALCAP ceramic described in U.S. Pat. No. 4,218,255 to Bajpai in ground or powdered form; the calcium phosphates described in U.S. Pat. No. 4,192,021; and the ALCAP ceramics described by Graves, G. A., et al., "Resorbable Ceramic Implants," J. Biomed. Mater. Res. Symp. 2 (Part I): 91, 1972.

The foregoing ceramics may be used alone or in combination. In particular, the ceramics can be combined to obtain a desired consistency and setting time for application to a surgical site. Resorbable and non-resorbable ceramics may be combined to provide a partially resorbable composition. For example, in certain applications, the ceramic stimulates bone development, and it may be desirable to formulate the compositions such that a major or minor portion of the ceramic is absorbed. One such mixture is a mixture of hydroxyapatite and $\beta$-tricalcium phosphate (70:30).

ALCAP ceramics useful in the present invention can be obtained by mixing calcium oxide, aluminum (III) oxide, and phosphorous pentoxide ($P_2O_5$) in weight ratios of about 35 to 40% CaO, about 45 to 55% $Al_2O_3$, and about 10 to 20% $P_2O_5$; compressing the mixture; and calcinining. A typical ALCAP ceramic is prepared from a 38:50:12 mixture of calcium oxide, aluminum oxide and phosphorus pentoxide which is calcined at 2400° F. for 12 hours and ground.

The bone substitutes used in the cement composition, in ground or powdered form, generally range in particle size from about 5 to 147 microns ($-400$ to $+100$ mesh). The particular size of the bone substitute has a direct effect on the cure rate. As the particle size of the bone substitute decreases, its total surface area increases and the cure rate is faster.

The surgical cement of the present invention can be formulated as a two-part package of the bone substitute and the acid which are mixed prior to surgery or as a pre-mixed one-part mixture of the ceramic and acid.

To cure the cement composition, it must be mixed with water or a water-containing medium. When water is added to the composition, two stages of setting are observed. During the first stage, the viscosity of the mixture increases rapidly and a paste is obtained which can be worked into a desired shape. During the second stage, the composition sets. While, in most instances, the compositions will be mixed with distilled or deionized water and formed into a paste for application, on occasion it may be desirable to mix the bone cement with blood or serum. In this regard, the cement compositions of the present invention have excellent hemostatic properties.

In some cases, it may be desirable to add metal salts to the cement compositions to enhance the cure rate. Calcium salts and, more particularly, calcium chloride and calcium sulfate are particularly useful for this purpose. The salts, when used, are usually added in an amount of about 5 to 20% by weight.

One of the most important advantages of the surgical elements of the present invention is that the compositions are cured through the reaction of the polyfunctional carboxylic acid and the bone substitute, and polymeric materials are not used to bind the bone substitute to the surgical site. In some cases, however, it may be desirable to add small amounts of polymeric materials, e.g., less than 10% by weight based on the total weight of the composition, to toughen the cement composition.

compositions with carbon fibers, bone lattice, cellulose fibers or bioabsorbable fibers as described in U.S. application Ser. No. 702,526, filed Feb. 19, 1985, now U.S. Pat. No. 4,604,097.

One preferred cement is a mixture of 70 parts hydroxyapatite and 30 parts tricalcium phosphate which is mixed in a 1:1 ratio with malic acid.

The invention is illustrated in more detail by reference to the following examples wherein, unless otherwise indicated, all percentages and ratios are by weight.

EXAMPLE 1

Varying amounts of setting agent and distilled water were mixed with ALCAP (0.392 ($Al_2O_3$): 0.544 (CaO): 0.064 ($P_2O_5$) mole ratio) having an average particle size of 5 to 38$\mu$ (−400 mesh) to determine the optimum composition in terms of setting time and hardness. Using the optimized compositions shown in Table 1, cements were prepared and tested for set time and hardness. Distilled or deionized water was added to each ALCAP/acid mixture and the mixture was then stirred with a spatula for 1 minute. The cement was allowed to set and periodically observed for hardness by pressing the cement with the edge of a spatula. A grade of one (1) was assigned to a toothpaste consistency and a grade of 10 to a hard consistency. The results are shown in Table 1.

TABLE 1

| Setting Agent | Weight (g) | ALCAP Powder (g) | Water (ml) | Hardness Minutes | | | | | | |
|---|---|---|---|---|---|---|---|---|---|---|
| | | | | 15 | 30 | 45 | 60 | 75 | 90 | 105 |
| Fumaric Acid | 0.25 | 1.0 | 0.6 | 8 | 9 | 10 | 10 | 10 | 10 | 10 |
| Malic Acid | 0.50 | 1.0 | 0.5 | 10 | 10 | 10 | 10 | 10 | 10 | 10 |
| Oxalo-Acetic Acid | 0.25 | 1.0 | 0.5 | 1 | 1 | 2 | 2 | 3 | 3 | 4 |
| α-Ketoglutaric Acid | 0.5 | 1.0 | 0.5 | 8 | 9 | 10 | 10 | 10 | 10 | 10 |
| α-Ketoglutaric Acid Citric Acid | 0.35 0.15 | 1.0 | 0.5 | 7 | 8 | 9 | 10 | 10 | 10 | 10 |
| α-Ketoglutaric Acid Citric Acid | 0.40 0.10 | 1.0 | 0.5 | 8 | 9 | 10 | 10 | 10 | 10 | 10 |

EXAMPLE 2

Using the same procedure and evaluation as in Example 1, cements containing hydroxyapatite powder (−400 to +30 mesh) obtained from Orthomatrix, Inc. Dublic, Ohio, were prepared, optimized and observed for hardening. The results are shown in Table 2.

TABLE 2

| Setting Agent | Weight (g) | Hydroxyapatite (g) | Water (ml) | Hardness Minutes | | | | | | |
|---|---|---|---|---|---|---|---|---|---|---|
| | | | | 15 | 30 | 45 | 60 | 75 | 90 | 105 |
| Fumaric Acid | 0.25 | 1.0 | 0.4 | 8 | 9 | 10 | 10 | 10 | 10 | 10 |
| Malic Acid | 0.30 | 1.0 | 0.3 | 10 | 10 | 10 | 10 | 10 | 10 | 10 |
| Oxalo-Acetic Acid | 0.25 | 1.0 | 0.4 | 1 | 1 | 1 | 1 | 1 | 2 | 2 |
| α-Ketoglutaric Acid | 0.50 | 1.0 | 0.3 | 8 | 9 | 10 | 10 | 10 | 10 | 10 |
| α-Ketoglutaric Acid Citric Acid | 0.35 0.15 | 1.0 | 0.3 | 7 | 8 | 8 | 9 | 9 | 10 | 10 |
| α-Ketoglutaric Acid Citric Acid | 0.40 0.10 | 1.0 | 0.3 | 8 | 9 | 10 | 10 | 10 | 10 | 10 |

For this purpose, polylactic acid, polymethacrylic acid or polyacrylic acid can be used.

The compositions of the present invention can be used in orthopaedic, oral and maxillofacial surgery. The compositions can be used in making bone grafts, bone scaffolds, bone replacements or protheses such as bone plates and the like. These materials may be non-bioabsorbable or totally or partially bioabsorbable. In making bone replacements, it may be desirable to reinforce the

EXAMPLE 3

Non-resorbable bone cement compositions containing hydroxyapatite (HA) were prepared by mixing Bio Gel hydroxyapatite (HA) powder having a particle size range of 5$\mu$ to 38$\mu$ (a product of Bio Rad Labs, Richmond, Calif.) with organic acids in the volume ratios shown in Table 3 below. The compositions were mixed with water and allowed to set and evaluated for their hardness at 15 minute intervals. Hardness was evaluated on a scale of 1 to 10 as in Example 1.

TABLE 3

| Test Materials | Weight Ratio in Paste | Degree of Hardness Time in Minutes | | | |
|---|---|---|---|---|---|
| | | 15 | 30 | 45 | 60 |
| HA: citric acid (powder) | 1:1 | 1 | 1 | 1 | 2 |
| HA: α-ketoglutaric acid (powder) | 1:3 | 7 | 8 | 9 | 10 |
| HA: succinic acid (powder) | 1:1 | 1 | 2 | 3 | 4 |

EXAMPLE 4

Two hundred grams of bone flour obtained from ICN Nutritional Biochemicals, Cleveland, Ohio, were treated according to the following procedure:

The bone flour was placed in a 100 mls. flask and washed four times with 500 mls. petroleum ether. The mixture was continuously stirred for each wash period of 30 minutes and filtered after each wash. The product was then washed four times with 500 mls. of 2% wt./vol. potassium hydroxide, stirred and filtered and washed four times with 500 mls. of deionized water, stirred and filtered. Finally, the bone flour was washed four times with 500 mls. of acetone, stirred and filtered.

The petroleum ether removes lipids from the flour, potassium hydroxide (KOH) removes protein and carbohydrates, and acetone removes water. Immediately after this treatment, a protein test is run to ensure that the recovered mineral flour is free of protein.

Elemental Analysis of Treated Bone Flour (200–250 particle mesh) by Inductively Coupled Plasma (I.C.P.) gives the following results expressed in weight percent.

| Element | I.C.P. Analysis |
|---|---|
| Si | 0.1 |
| P | major |
| Al | 0.04 |
| Fe | 0.005 |
| Mg | 0.7 |
| Ca | major |
| Na | 0.6 |
| K | 0.4 |
| Mo | 0.009 |
| Zn | 0.02 |
| Ba | 0.009 |
| Sr | 0.002 |
| Mn | 0.005 |
| Cu | 0.005 |
| Ti | 0.005 |
| B | 0.005 |
| Cr | 0.005 |

Surgical cements were prepared by mixing the bone mineral with polyfunctional carboxylic acids in the ratios shown in Table 4 and water to obtain a paste-like consistency. The samples were evaluated for their hardness at 15 minute intervals as in Example 1. Generally speaking, these compositions exhibit a faster setting and hardening time than the hydroxyapatite compositions shown in Example 3.

TABLE 4

| Test Materials | Ratio in Paste | Degree of Hardness Time in Minutes | | | |
|---|---|---|---|---|---|
| | | 15 | 30 | 45 | 60 |
| Bone mineral: citric acid | 1:1 | 1 | 2 | 3 | 4 |
| Bone mineral: α-ketoglutaric | 1:1 | 9 | 10 | 10 | 10 |

TABLE 4-continued

| Test Materials | Ratio in Paste | Degree of Hardness Time in Minutes | | | |
|---|---|---|---|---|---|
| | | 15 | 30 | 45 | 60 |
| acid | | | | | |
| Bone mineral: succinic acid | 1:1 | 3 | 4 | 5 | 6 |

EXAMPLE 5

Resorbable surgical cements were prepared by mixing β-tricalcium phosphate (TCP) and polyfunctional organic acids in the ratios shown in Table 5 below with water to achieve a paste-like consistency. The samples were evaluated for their hardness as in Example 1. The results are shown in Table 5 below.

TABLE 5

| Test Materials | Ratio in Paste | Degree of Hardness Time in Minutes | | | |
|---|---|---|---|---|---|
| | | 15 | 30 | 45 | 60 |
| TCP: citric acid (powder) | 1:1 | 2 | 2 | 3 | 4 |
| TCP: α-ketoglutaric acid (powder) | 2:1 | 8 | 9 | 10 | 10 |
| TCP: succinic acid (powder) | 1:1 | 2 | 3 | 4 | 4 |
| TCP: α-ketoglutaric acid: citric acid | 1:0.35:0.15 | 7 | 8 | 8 | 8 |
| TCP: α-ketoglutaric acid: citric acid | 1:0.4:0.1 | 8 | 8 | 8 | 9 |

EXAMPLE 6

Bone cements in accordance with the present invention were prepared and used to fill drill holes (2 mm diameter) in the tibias of rabbits. The rabbits were postoperatively treated with tetracyclines to label bone activity. For comparison, bone ingrowth into an empty drill hole and drill holes filled with dry, uncured bone substitute were also observed. The results are summarized below.

Control Drill Holes—Bone ingrowth into empty drill holes varied among the examined samples. Some samples showed extensive peri and endosteal trabecular bone ingrowth filling the drill holes. Others showed only endosteal bone ingrowth that incompletely filled the holes.

ALCAP (−400 mesh)/α-ketoglutarate (2:1)—Some peri and endosteal trabecular bone ingrowth was observed around the periphery of these implant materials, and there was some infiltration of new bone into the implants. In the areas of bone ingrowth, there seemed to be some resorption or incorporation of the implant material. The cores of the samples remained free of bone ingrowth at four weeks and showed no signs of resorption.

ALCAP (−400 mesh)—The tissue response to this material was identical to that of the ALCAP/α-ketoglutarate material.

HA (40–50 mesh) a product of Orthomatrix, Inc., Dublin, Ohio/α-ketoglutarate (2:1)—Peri and endosteal trabecular bone growth was observed that infiltrated the spaces between the large particles of HA. There was no sign of resorption of the HA material. Good apposition of trabecular bone and HA particles was observed.

HA (Spray Dried) (Orthomatrix)/α-ketoglutarate (2:1)—Little peri and endosteal trabecular bone ingrowth was observed around the peripheries of these samples, and there was no infiltration into the cores of the samples. There was little or no resorption of this material.

HA (Spray Dried) (Orthomatrix)—The tissue response to this material was similar to that of the HA (Spray Dried)/α-ketoglutarate material.

TCP/α-ketoglutarate (2:1)—Large amounts of peri and endosteal trabecular bone ingrowth were observed that seemed to extend into the core of the sample that was examined. Large amounts of resorption or incorporation were taking place since the only observable implant material remaining was at the center of the drill hole.

The foregoing results show that all of the materials studied remained in place in the drill holes sufficiently for tissue ingrowth to occur. Also, all of the materials showed some degree of trabecular bone ingrowth that was comparable to the ingrowth observed in the control drill holes. None of the materials exhibited an extensive inflammatory response or noticeably inhibited bone ingrowth. The use of α-ketoglutaric acid as a setting agent had no noticeable effect on tissue response.

Having described the invention in detail and by reference to specific examples thereof, it will be apparent that numerous variations and modifications are possible without departing from the spirit and scope of the following claims.

What is claimed is:

1. A surgical cement consisting essentially of a bone substitute and a water soluble, polyfunctional carboxylic acid, said acid containing 2 to 10 carbon atoms and being present in an amount of about 25 to 100 parts by weight per 100 parts by weight of said bone substitute.

2. The surgical cement of claim 1 wherein said acid contains 2 to 4 carboxyl groups.

3. The surgical cement of claim 2 wherein said polyfunctional carboxylic acid contains 2 to 6 carbon atoms.

4. The bone cement of claim 1 wherein said bone substitute is resorbable.

5. The bone cement composition of claim 1 wherein said bone substitute is non-resorbable.

6. The bone cement composition of claim 1 wherein said bone substitute is beta-tricalcium phosphate.

7. The bone cement composition of claim 1 wherein said bone substitute is hydroxyapatite.

8. The bone cement composition of claim 1 wherein said bone substitute is milled freeze dried bone.

9. The bone cement composition of claim 1 wherein said bone substitute is a synthetic calcium-containing material selected from the group consisting of calcium aluminates, calcium phosphates and alumino-calcium oxidephosphorous pentoxide ceramics.

10. The bone cement composition of claim 1 wherein said polyfunctional carboxylic acid exhibits a pK less than 5.61 and greater than 3.08.

11. The bone cement composition of claim 1 wherein said polyfunctional carboxylic acid is an acid on the Kreb's cycle.

12. The bone cement composition of claim 11 wherein said polyfunctional carboxylic acid includes α-ketoglutaric acid.

13. The bone cement composition of claim 1 wherein said polyfunctional carboxylic acid includes fumaric acid.

14. The bone cement composition of claim 1 wherein said polyfunctional carboxylic acid includes malic acid.

15. The bone cement composition of claim 12 wherein said polyfunctional carboxylic acid is a combination of citric acid and α-ketoglutaric acid.

16. The bone cement composition of claim 1 further including a calcium salt.

17. The surgical cement composition of claim 1 further including a reinforcing fiber.

18. The surgical cement composition of claim 1 wherein said bone substitute has a particle size less than 400 mesh.

19. A surgical cement consisting essentially of 100 parts by weight of a bone substitute, 25 to 100 parts by weight of a water soluble polyfunctional carboxylic acid having to 10 carbon atoms, and up to 10 parts by weight of a polymeric material, said bone substitute being a resorbable or non-resorbable material selected from the group consisting of beta-tricalcium phosphate, hydroxyapatite, milled freeze dried bone, calcium aluminate, calcium phosphate and alumino-calcium oxidephosphorous pentoxide ceramic, and said polyfunctional carboxylic acid contains 2 to 6 carbon atoms and 2 to 4 carboxyl groups and exhibits a pK less than 5.61 and greater than 3.08.

20. The surgical cement of claim 19 wherein said polyfunctional carboxylic acid is α-ketoglutaric acid.

21. A surgical cement consisting essentially of 100 parts by weight of a bone substitute, 25 to 100 parts by weight of a water soluble polyfunctional carboxylic acid having up to 10 carbon atoms, and up to 10 parts by weight of a polymeric material, said bone substitute being a resorbable or non-resorbable material selected from the group consisting of beta-tricalcium phosphate, hydroxyapatite, milled freeze dried bone, calcium aluminate, calcium phosphate and alumino-calcium oxidephosphorous pentoxide ceramic, and said polyfunctional carboxylic acid containing 2 to 6 carbon atoms and 2 to 4 carboxyl groups and exhibiting a pK less than 5.61 and greater than 3.08 and said polymeric material being selected from the group consisting of polylactic acid, polyacrylic acid and polymethacrylic acid.

* * * * *